United States Patent [19]

Cusic et al.

[11] 3,937,701

[45] Feb. 10, 1976

[54] 1-(10-CYANO/HALO-5H-DIBENZO[A,D]CYCLOHEPTEN-5-YL)-4-[(PYRIDYLMETHYLENE)AMINO]PIPERAZINES

[75] Inventors: John W. Cusic, Skokie; Charles R. Ellefson, Chicago, both of Ill.

[73] Assignee: G. D. Searle & Co., Chicago, Ill.

[22] Filed: Nov. 1, 1974

[21] Appl. No.: 519,939

[52] U.S. Cl.... 260/240 G; 260/240 TC; 260/240.8; 260/268 TR; 260/999; 424/250
[51] Int. Cl.$^2$................................. C07D 401/12
[58] Field of Search ...... 260/240 TC, 240.8, 240 G, 260/268 TR

[56] References Cited
UNITED STATES PATENTS

| | | | |
|---|---|---|---|
| 3,377,344 | 4/1968 | Cusic et al. | 260/240 TC |
| 3,573,288 | 3/1971 | Cusic et al. | 260/240 TC |

OTHER PUBLICATIONS

Hoffmann–La–Roche, Chem. Abstracts, 64, (1966), col. 5024.

*Primary Examiner*—Arthur P. Demers
*Attorney, Agent, or Firm*—John M. Brown

[57] ABSTRACT

Preparation and the anticonvulsant utility of 1-(10-cyano/halo-5H-dibenzo[a,d]cyclohepten-5-yl)-4-[(pyridylmethylene)amino]piperazines are disclosed.

12 Claims, No Drawings

1-(10-CYANO/HALO-5H-DIBENZO[A,D]CYCLOHEPTEN-5-YL)-4-[(PYRIDYLMETHYLENE)AMINO]PIPERAZINES

This invention relates to 1-(10-cyano/halo-5H-dibenzo[a,d]cyclohepten-5-yl)-4-[(pyridylmethylene)amino]=piperazines, and intermediates thereto. More particularly, this invention provides new, useful, and unobvious chemical compounds of the formula

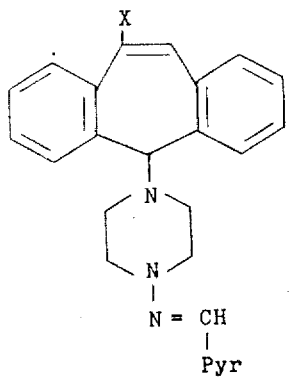

wherein X represents halogen or cyano and Pyr represents pyridyl optionally substituted by fewer than 5 alkyls.

Among the halogens comprehended by X in the foregoing formula, those having an atomic number greater than 9 and less than 53 (i.e., chlorine and bromine) are preferred. As to the optionally-alkylated pyridyls comprehended by Pyr, pyridyl and pyridyl substituted by lower alkyl — which is to say methyl, ethyl, propyl, isopropyl, butyl, isobutyl, sec.-butyl, tert.-butyl, pentyl, neopentyl, hexyl, isohexyl, heptyl, and like monovalent, saturated, acyclic, straight- or branched-chain hydrocarbon groupings of the formula $$-C_nH_{2n+1}$$

wherein $n$ represents a positive integer less than 8 — are preferred. The point of attachment of the pyridyl nucleus to the adjacent methylene and the disposition of any alkyl(s) substituting the nucleus, both with respect to said point of attachment and to each other (when a plurality are present), is acritical; 2-pyridyl, 3-pyridyl, and 4-pyridyl, each optionally alkylated ad libitum, are all within the purview of this invention.

Equivalent to the enformulated bases for the purposes of this invention are non-toxic acid addition salts thereof having the formula

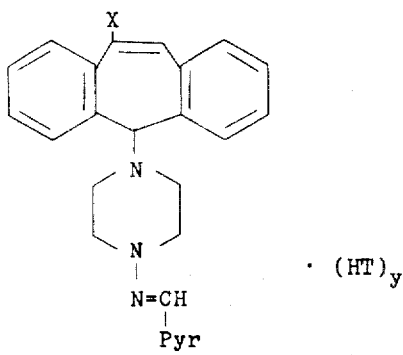

wherein X and Pyr are defined as before; T represents 1 equivalent of an anion — for example, chloride, bromide, iodide, nitrate, phosphate, sulfate, sulfamate, methyl sulfate, ethyl sulfate, benzenesulfonate, toluenesulfonate, acetate, lactate, succinate, maleate, tartrate, citrate, gluconate, ascorbate, benzoate, cinnamate, or the like — which, in combination with the cationic portion of a salt aforesaid, is neither biologically nor otherwise incompatible; and $y$ represents a positive integer less than 4, its precise value being dependent upon the number of basic nitrogens involved in salt formation.

The subject compounds are useful by reason of their valuable biological properties. Thus, for example, they are anticonvulsants, as can be demonstrated by the results of a standardized test for their capacity to prevent the convulsions induced in mice by electoral shock. The procedure is a modification of the one described by E. A. Swinyard et al., J. Pharmacol. Exp. Therap., 106, 319 (1952), whereby 50 mg per kg of the compound to be tested, dissolved or suspended in 10 ml of a vehicle such as saline or corn oil, is administered intragastrically to each of 10 mice. At a specific time after the administration of the test compound (ordinarily 2½ hours), each mouse is challenged with a current of 2 mA, delivered via corneal electrodes, for 0.2 seconds. This current is sufficient to induce maximal electroshock seizures in 100% of control animals. A compound is considered active in this test if the hind limb tonic extensor component of the seizure pattern is abolished in at least 20% of the animals in the group to which the compound is administered. By way of illustration, the products of Examples 2, 4, 9, and 10 hereinafter were found active at doses ranging from 3 to 6 mg per kg in this test.

Those skilled in the art will recognize that observations of activity in standardized tests for particular biological effects are fundamental to the development of valuable new drugs, both veterinary and human.

Preparation of the compounds of this invention proceeds by heating a 1-(10-cyano/halo-5H-dibenz[a,d]cyclohepten-5-yl)-4-piperazineamine with an aldehyde of the formula (in which Pyr retains the meaning previously assigned)

Pyr-CHO in 2-propanol, using a small amount of acetic acid as a catalyst if desired. 1-(10-Cyano/halo-5H-dibenz[a,d]=cyclohepten-5-yl)-4-piperazineamine is prepared by heating a 2-butanone solution of 5-chloro-10-cyano/halo-5H-dibenz=[a,d]cycloheptene with N-nitrosopiperazine in the presence of potassium carbonate and reducing the resultant 1-(10-cyano/halo-5H-dibenz[a,d]cyclohepten-5-yl)-4-nitropiperazine by heating it with zinc dust in acetic acid. 5-Chloro-10-halo-5H-dibenz[a,d]cycloheptene can be prepared by heating 10-halo-5H-dibenz[a,d]cyclohepten-5-one with sodium tetrahyydroborate(1-) in ethanol, thereby reducing the carbonyl to hydroxyl, then replacing the hydroxyl with chloro by heating the cycloheptenol with thionyl chloride in chloroform or with hydrogen chloride in benzene.

Conversion of the bases of this invention to corresponding acid addition salts is accomplished by admixture with 3 or fewer equivalents of any of various inorganic and strong organic acids, the anionic portion of which conforms to T as hereinabove defined. The salts, in turn, are converted to corresponding bases by contacting with excess alkali.

The following examples describe in detail compounds illustrative of the present invention and methods which have been devised for their preparation. It will be apparent to those skilled in the art that many modifications, both of materials and of methods, may be practiced without departing from the purpose and intent of this disclosure. Throughout the examples hereinafter set forth, temperatures are given in degrees centigrade and relative amounts of materials in parts by weight, except as otherwise noted.

EXAMPLE 1

A. Anhydrous hydrogen chloride is passed into a mixture of approximately 27 parts of 10-bromo-5H-dibenzo=[a,d]cyclohepten-5-ol [Arzneimittel-Forsch., 19, 1936 (1969)] and 180 parts of anhydrous benzene for 1 hour. The organic phase is thereupon separated, dried over anhydrous calcium sulfate, and stripped of solvent by vacuum distillation. The residue is 10-bromo-5-chloro-5H-dibenzo[a,d]=cycloheptene.

B. To a solution of approximately 29 parts of 10-bromo-5-chloro-5H-dibenzo[a,d]cycloheptene in 325 parts of 2-butanone is added a solution of 14 parts of N-nitrosopiperazine in 40 parts of 2-butanone. The resultant mixture is stirred for ½ hour, whereupon 30 parts of anhydrous potassium carbonate is introduced; and the mixture thus obtained is heated at the boiling point under reflux with stirring for 4 hours and thereupon allowed to stand at room temperatures overnight. Insoluble solids are filtered out, and the filtrate is stripped of solvent by vacuum distillation. The solid residue is consecutively washed with ethanol and hexane, then air-dried. The colorless crystalline product thus isolated is 1-(10-bromo-5H-dibenzo[a,d]cyclohepten-5-yl)-4-nitrosopiperazine.

C. To a suspension of 20 parts of 1-(10-bromo-5H-dibenzo[a,d]cyclohepten-5-yl)-4-nitrosopiperazine in 1400 parts of anhydrous ether is slowly added 7 parts of lithium tetrahydroaluminate(1-). The resultant mixture is stirred at room temperatures for 5 hours, then cooled to around 5° and maintained thereat while a solution of 14 parts of water in 25 parts of tetrahydrofuran, 18 parts of aqueous 25% sodium hydroxide, and 14 parts of water are consecutively introduced. Insoluble solids are removed by filtration and washed with tetrahydrofuran. The washings and filtrate are combined, dried over anhydrous magnesium sulfate, and stripped of solvent by vacuum distillation. The residual yellow solid is crystallized from a mixture of tetrahydrofuran and hexane to give 1-(10-bromo-5H-dibenzo[a,d]cyclohepten-5-yl)-4-piperazineamine as colorless crystals melting at 187.5°–190.5°.

D. A mixture of 80 parts of 1-(10-bromo-5H-dibenzo[a,d]cyclohepten-5-yl)-4-piperazineamine, 32 parts of 2-pyridinecarboxaldehyde, 1 part of glacial acetic acid, and 650 parts of 2-propanol is heated at the boiling point under reflux for 6 hours, then chilled. The crystalline precipitate which forms is removed by filtration, washed with hexane, and air-dried. The brown material thus isolated is recrystallized from 2-propanol, washed with hexane, and dried in vacuo to give 1-(10-bromo-5H-dibenzo[a,d]=cyclohepten-5-yl)-4-[(2-pyridylmethylene)amino]piperazine as beige crystals melting at 166.5°–168°. The product has the formula

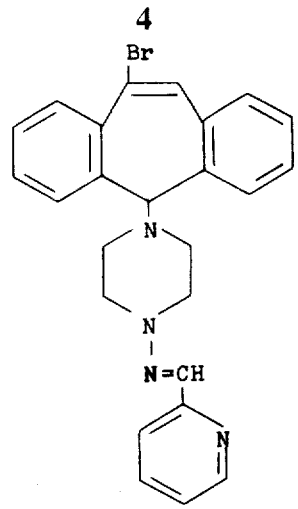

EXAMPLE 2

A mixture of 60 parts of 1-(10-bromo-5H-dibenzo[a,d]cyclohepten-5-yl)-4-piperazineamine, 22 parts of 3-pyridinecarboxaldehyde, 1 part of glacial acetic acid, and 475 parts of 2-propanol is heated at the boiling point under reflux for 6 hours, then stripped of solvent by vacuum distillation. The residual oil solidifies on mixing with hexane. Insoluble solids are removed by filtration and recrystallized from a mixture of tetrahydrofuran and hexane to give 1-(10-bromo-5H-dibenzo[a,d]=cyclohepten-5-yl)-4-[(3-pyridylmethylene)amino]piperazine, which can be further purified by recrystallization from absolute ethanol. The product is isolated thus as light beige crystals which, dried in vacuo, melt at 162.5°–165°.

EXAMPLE 3

Substitution of 32 parts of 4-pyridinecarboxaldehyde for the 2-pyridinecarboxaldehyde called for in Example 1D affords, by the procedure there detailed, 1-(10-bromo-5H-dibenzo[a,d]cyclohepten-5-yl)-4-[(4-pyridylmethylene)amino]=piperazine. The product is thus isolated as a pale yellow solid melting at 208°–211.5°.

EXAMPLE 4

A mixture of 67 parts of 1-(10-bromo-5H-dibenzo=[a,d]cyclohepten-5-yl)-4-piperazineamine, 32 parts of 6-methyl-2-pyridinecarboxaldehyde, 1 part of glacial acetic acid, and 560 parts of 2-propanol is heated at the boiling point under reflux for 5½ hours, then stripped of solvent by vacuum distillation. The residue, recrystallized from absolute ethanol, affords 1-(10-bromo-5H-dibenzo[a,d]=cyclohepten-5-yl)-4-[(6-methyl-2-pyridylmethylene)amino]=piperazine as light beige crystals which, dried in vacuo at 80°, melt at 160.5°–163°.

EXAMPLE 5

A mixture of 67 parts of 1-(10-bromo-5H-dibenzo=[a,d]cyclohepten-5-yl)-4-piperazineamine, 36 parts of 5-ethyl-2-pyridinecarboxaldehyde, 1 part of glacial acetic acid, and 560 parts of 2-propanol is heated at the boiling point under reflux for 6 hours, then stripped of solvent by vacuum distillation. The residue is 1-(10-bromo-5H-dibenzo[a,d]cyclohepten-5-yl)-4-[(5-ethyl- 2-pyridylmethylene)=amino]piperazine.

EXAMPLE 6

A. A mixture of 48 parts of 10-chloro-5H-dibenzo=λ[a,d]cyclohepten-5-one (U.S. Pat. No. 3,297,763) and 325 parts of absolute ethanol is heated to 60°, whereupon 16 parts of sodium tetrahydroborate (1-) is stirred in at a rate such that the temperature does not exceed 65°. When the addition is complete, the reaction mixture is stirred at 70° for 2 hours and then poured into 1500 parts of a mixture of ice and water. Insoluble solids are filtered out and extracted with ether, the filtrate is saturated with sodium chloride and then extracted with ether, and the two extracts are combined, washed with water, dried over anhydrous magnesium sulfate, and stripped of solvent by vacuum distillation. The residue is 10-chloro-5H-dibenzo[a,d]cyclohepten-5-ol.

B. To a mixture of 5 parts of 10-chloro-5H-dibenzo[a,d]cyclohepten-5-ol with 50 parts of chloroform is slowly added a solution of 8 parts of thionyl chloride in 5 parts of chloroform. The resultant mixture is heated at the boiling point under reflux with stirring for 4 hours, then stripped of solvent by vacuum distillation. The residue is 5,10-dichloro-5H-dibenzo[a,d]=cycloheptene.

C. To a solution of 24 parts of 5,10-dichloro-5H-dibenzo[a,d]cycloheptene in 325 parts of 2-butanone is added a solution of 14 parts of N-nitrosopiperazine in 40 parts of 2-butanone. The resultant mixture is stirred for 1 hour, whereupon 30 parts of anhydrous potassium carbonate is introduced. The mixture thus obtained is heated at the boiling point under reflux with stirring for 6 hours, then stripped of solvent by vacuum distillation. The residue is 1-(10-chloro-5H-dibenzo[a,d]=cyclohepten-5-yl)-4-nitrosopiperazine, which can be further purified by washing with hexane.

D. Substitution of 18 parts of 1-(10-chloro-5H-dibenzo[a,d]cyclohepten-5-yl)-4-nitrosopiperazine for the 1-(10-bromo-5H-dibenzo[a,d]cyclohepten-5-yl)-4-nitrosopiperazine called for in Example 1C affords, by the procedure there detailed, 1-(10-chloro-5H-dibenzo[a,d]=cyclohepten-5-yl)-4-piperazineamine.

E. A mixture of 73 parts of 1-(10-chloro-5H-dibenzo[a,d]cyclohepten-5-yl)-4-piperazineamine, 32 parts of 2-pyridinecarboxaldehyde, 1 part of glacial acetic acid, and 650 parts of 2-propanol is heated at the boiling point under reflux for 6 hours, then stripped of solvent by vacuum distillation. The residue is 1-(10-chloro-5H-dibenzo[a,d]cyclohepten-5-yl)-4-[(2-pyridylmethyleneamino]=piperazine.

EXAMPLE 7

A. To a mixture of 19 parts of 5-chloro-5H-dibenzo[a,d]cycloheptene-10-carbonitrile [Arzeimittel-Forsch., 19, 1936 (1969)], 20 parts of powdered anhydrous potassium carbonate, and 160 parts of 2-butanone is added a solution of 10 parts of N-nitrosopiperazine in 40 parts of 2-butanone. The resultant mixture is heated at the boiling point under reflux with stirring for 8 hours, then allowed to stand at room temperatures until precipitation is complete. The precipitate is filtered off and consecutively washed with 2-butanone and 2-propanone. Washings and the filtrate are combined and stripped of solvent by vacuum distillation. The residual thick oil crystallizes from absolute ethanol. The product thus isolated is 5-(4-nitroso-1-piperazinyl)-5H-dibenzo[a,d]cycloheptene-10-carbonitrile melting at 173°–178°.

B. Approximately 500 parts of water is slowly added to a solution of 98 parts of 5-(4-nitroso-1-piperazinyl)-5H-dibenzo[a,d]cycloheptene-10-carbonitrile in 1200 parts of glacial acetic acid. To the resultant mixture is added, at a rate such that the temperature does not exceed 35°, approximately 150 parts of zinc dust. When the addition is complete, the reaction mixture is stirred at 28°–30° for 1 hour, whereupon insoluble solids are filtered out and washed with 300 parts of 65% acetic acid. Washings and filtrate are combined and diluted with 3 volumes of water. The solution thus obtained is cooled to 5°–10° and maintained thereat while sufficient 30% ammonium hydroxide is added to induce alkalinity. The resultant mixture is extracted with chloroform. The chloroform extract is dried over anhydrous potassium carbonate and stripped of solvent by vacuum distillation. The residual viscous oil crystallizes from hexane to give 5-(4-amino-1-piperazinyl)-5H-dibenzo[a,d]cycloheptene-10-carbonitrile as a colorless solid which, dried in air, melts at 137°–146°.

C. A mixture of 40 parts of 5-(4-amino-1-piperazinyl)-5H-dibenzo[a,d]cycloheptene-10-carbonitrile, 50 parts of 2-pyridinecarboxaldehyde, 3 parts of glacial acetic acid, and 400 parts of 2-propanol is heated at the boiling point under reflux for 5 hours, then refrigerated until precipitation is complete. Insoluble solids are removed by filtration, consecutively washed with absolute ethanol and hexane, and air-dried. Recrystallization of this material from a mixture of chloroform and hexane affords 5-[4-(2-pyridylmethylene)amino-1-piperazinyl]-5H-dibenzo[a,d]cycloheptene-10-carbonitrile as a light tan solid which, dried in air, melts at 182.5°–184°.

EXAMPLE 8

Substitution of 50 parts of 3-pyridinecarboxaldehyde for the 2-pyridinecarboxaldehyde called for in Example 7C affords, by the procedure there detailed, 5-[4-(3-pyridylmethylene)amino-1-piperazinyl]-5H-dibenzo[a,d]=cycloheptene-10-carbonitrile. The light yellow crystalline product melts at 241°–244°.

EXAMPLE 9

Substitution of 50 parts of 4-pyridinecarboxaldehyde for the 2-pyridinecarboxaldehyde called for in Example 7C affords, by the procedure there detailed, 5-[4-(4-pyridylmethylene)amino-1-piperazinyl]-5H-dibenzo=[a,d]cycloheptene-10-carbonitrile. The colorless product melts at 224.5°–227.5°.

EXAMPLE 10

A mixture of 30 parts of 5-(4-amino-1-piperazinyl)-5H-dibenzo[a,d]cycloheptene-10-carbonitrile, 21 parts of 6-methyl-2-pyridinecarboxaldehyde, 1 part of glacial acetic acid, and 250 parts of 2-propanol is heated at the boiling point under reflux with stirring for 4 hours, then stripped of solvent by vacuum distillation. The residue is crystallized from a mixture of tetrahydrofuran and hexane to give 5-{4-[(6-methyl-2-pyridylmethylene)amino]-1-piperazinyl}-5H-dibenzo[a,d]cycloheptene-10-carbonitrile as light brown crystals melting at 200°–202°.

EXAMPLE 11

A mixture of 30 parts of 5-(4-amino-1-piperazinyl)-5H-dibenzo[a,d]cycloheptene-10-carbonitrile, 17 parts of 5-ethyl-2-pyridinecarboxaldehyde, 1 part of glacial acetic acid, and 250 parts of 2-propanol is heated at the boiling point under reflux with stirring for 6 hours, then stripped of solvent by vacuum distillation. The residue is 5-{4-[(5-ethyl-2-pyridylmethylene)amino]-1-piperazinyl}-5H-dibenzo[a,d]cycloheptene-10-carbonitrile, which can be further purified by washing with hexane.

What is claimed is:

1. A compound of the formula

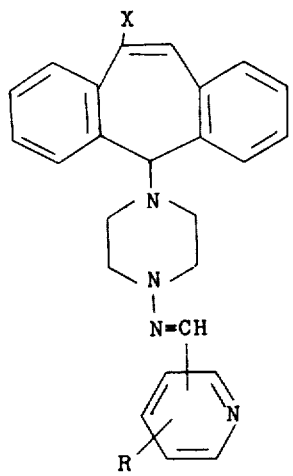

wherein X represents chlorine, bromine or cyano and R represents hydrogen or lower alkyl.

2. A compound according to claim 1 having the formula

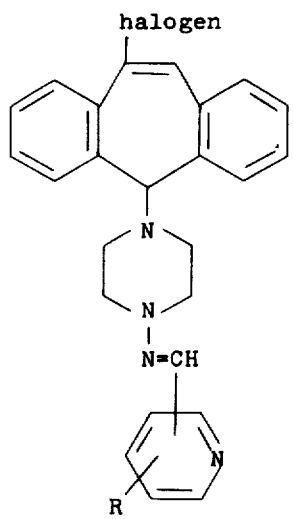

wherein the halogen called for is chlorine or bromine and R represents hydrogen or lower alkyl.

3. A compound according to claim 1 having the formula

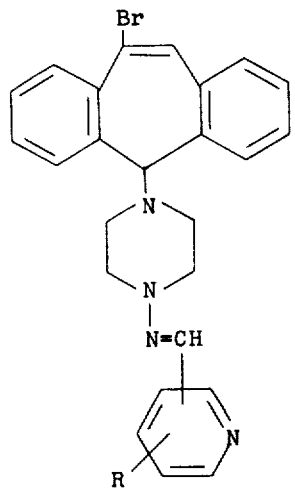

wherein R represents hydrogen or lower alkyl.

4. A compound according to claim 1 which is 1-(10-bromo-5H-dibenzo[a,d]cyclohepten-5-yl)-4-[(6-methyl-2-pyridylmethylene)amino]piperazine.

5. A compound according to claim 1 having the formula

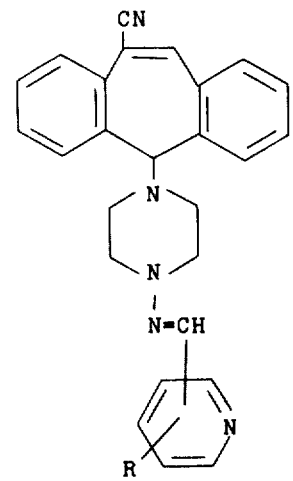

6. A compound according to claim 1 which is 1-(10-bromo-5H-dibenzo[a,d]cyclohepten-5-yl)-4-[(3-pyridylmethylene)amino]piperazine.

7. A compound according to claim 1 having the formula

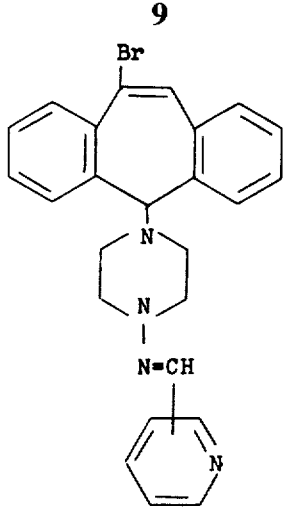

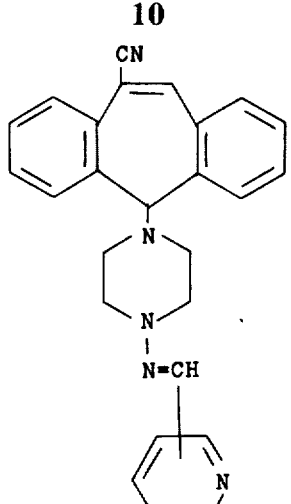

wherein R represents hydrogen or lower alkyl.

8. A compound according to claim 1 which is 5-{4-[(6-methyl-2-pyridylmethylene)amino]-1-piperazinyl}-5H-dibenzo[a,d]cycloheptene-10-carbonitrile.

9. A compound according to claim 1 having the formula

10. A compound according to claim 1 which is 5-[4-(4-pyridylmethylene)amino-1-piperazinyl]-5H-dibenzo=[a,d]cycloheptene-10-carbonitrile.

11. 1-(10-Bromo-5H-dibenzo[a,d]cyclohepten-5-yl)-4-piperazineamine.

12. 5-(4-amino-1-piperazinyl)-5H-dibenzo[a,d]=cycloheptene-10-carbonitrile.

* * * * *

UNITED STATES PATENT OFFICE
CERTIFICATE OF CORRECTION - Page 1 of 3

PATENT NO. : 3,937,701
DATED : Feb. 10, 1976
INVENTOR(S) : John W. Cusic and Charles R. Ellefson It is certified that error appears in the above-identified patent and that said Letters Patent are hereby corrected as shown below:

Column 2, line 53, "nitropiperazine" should read -- nitrosopiperazine --.

Column 2, line 57, "tetrahyydroborate" should read -- tetrahydroborate --.

Column 5, line 4, "dibenzo=λ" should read -- dibenzo= --.

Column 8, Claim 5 formula,

"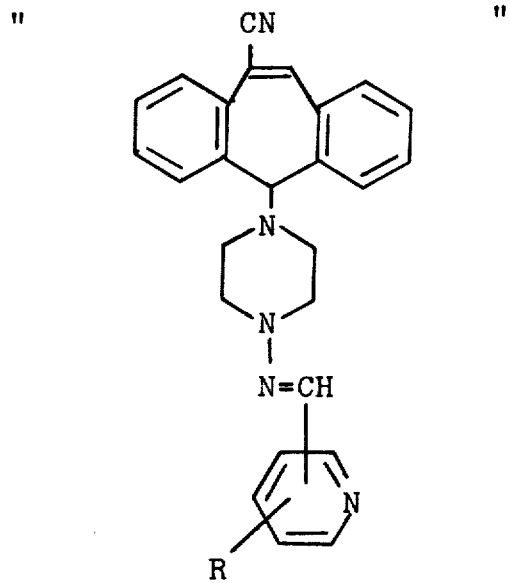"

should read --

(Contd.)

UNITED STATES PATENT OFFICE
CERTIFICATE OF CORRECTION - Page 2 of 3

PATENT NO. : 3,937,701
DATED : Feb. 10, 1976
INVENTOR(S) : John W. Cusic and Charles R. Ellefson It is certified that error appears in the above-identified patent and that said Letters Patent are hereby corrected as shown below:

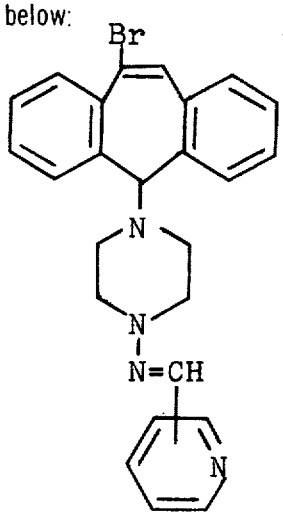

--.

Column 9, Claim 7 formula,

" 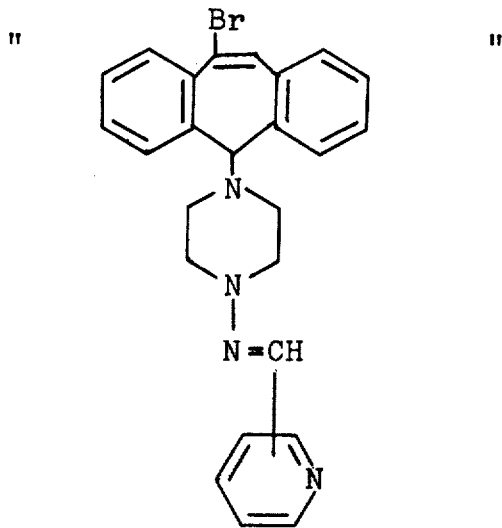 "

(Contd.)

UNITED STATES PATENT OFFICE
CERTIFICATE OF CORRECTION - Page 3 of 3

PATENT NO. : 3,937,701
DATED : Feb. 10, 1976
INVENTOR(S) : John W. Cusic and Charles R. Ellefson It is certified that error appears in the above-identified patent and that said Letters Patent are hereby corrected as shown below:

should read --

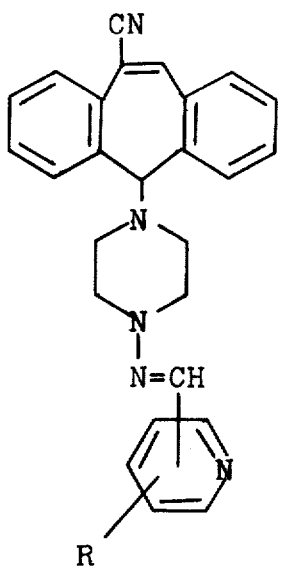

--.

Signed and Sealed this twenty-ninth Day of June 1976

[SEAL]

Attest:

RUTH C. MASON
*Attesting Officer*

C. MARSHALL DANN
*Commissioner of Patents and Trademarks*